(12) United States Patent
Demers et al.

(10) Patent No.: US 8,193,503 B2
(45) Date of Patent: Jun. 5, 2012

(54) METHOD OF DETECTING ORGANIC MATERIALS USING TERAHERTZ SPECTROSCOPY

(75) Inventors: Joseph R. Demers, Alhambra, CA (US); Ronald T. Logan, Jr., Pasadena, CA (US)

(73) Assignee: Emcore Corporation, Albuquerque, NM (US)

( * ) Notice: Subject to any disclaimer, the term of this patent is extended or adjusted under 35 U.S.C. 154(b) by 0 days.

(21) Appl. No.: 12/634,422

(22) Filed: Dec. 9, 2009

(65) Prior Publication Data

US 2011/0133090 A1    Jun. 9, 2011

(51) Int. Cl.
   *G01J 5/02* (2006.01)
(52) U.S. Cl. .................................................. 250/341.8
(58) Field of Classification Search ............... 250/341.8
   See application file for complete search history.

(56) References Cited

U.S. PATENT DOCUMENTS

2008/0128618 A1* 6/2008 Rahman et al. ............... 250/332

OTHER PUBLICATIONS

Withayachumnankul et al., T-Ray Sensing and Imaging, Aug. 2007, Proceedings of IEEE, vol. 95, 1528-1558.*
Korter et al., Terahertz spectroscopy of solid serine and cysteine, Chemical Physics Letters, vol. 418, pp. 68-70.*
Koreter et al., Terahertz Spectroscopy of Solid Serine and Cysteine, 2006, Chemical Physics Letters, vol. 418, pp. 68-70.*
Go et al., "Dynamics of a small globular protein in terms of low-frequency vibrational modes." Proceedings of the National Academy of Sciences of the United States of America, vol. 80, pp. 3696-3700. Jun. 1983. Natl. Acad. Sci. USA: Washington, DC.
Brooks et al., "Normal modes for specific motions of macromolecules: Application to the hinge-bending mode of lysozyme." Proceedings of the National Academy of Sciences of the United States of America, vol. 82, pp. 4995-4999. Aug. 1985. Natl. Acad. Sci. USA: Washington, DC.
Hill et al., "Corona poling of nonlinear polymer thin films for electro-optic modulators." Applied Physics Letters, vol. 65, No. 14, Oct. 3, 1994. pp. 1733-1735. American Institute of Physics: Melville, NY.
Saito et al., "First Principles Calculation of Terahertz Vibrational Modes of a Disaccharide Monohydrate Crystal of Lactose." Japanese Journal of Applied Physics, vol. 45, No. 43, 2006. pp. L1156-L1158. The Japan Society of Applied Physics: Tokyo, Japan.
Allis et al., "Assignment of the lowest-lying THz absorption signatures in biotin and lactose monohydrate by solid-state density functional theory." Chemical Physics Letters, vol. 440, Nos. 4-6, Jun. 2007. pp. 203-209. Elsevier: Amsterdam, Netherlands.
Yun et al., "Alignment of cellulose chains of regenerated cellulose by corona poling and its piezoelectricity." Journal of Applied Physics, vol. 103, 083301, 2008. pp. 083301-1-083301-4. American Institute of Physics: Melville, NY.
Chen et al., "Comparison of continuous-wave terahertz wave generation and bias-field-dependent saturation in GaAs: O and LT-GaAs antennas." Optics Letters, vol. 34, No. 7, Apr. 1, 2009. pp. 935-937. Optical Society of America: Washington, DC.

* cited by examiner

*Primary Examiner* — Christine Sung

(57) ABSTRACT

Disclosed herein are methods of detecting organic materials, and more particularly, methods of detecting organic materials using terahertz spectroscopy. The method of detecting organic material using terahertz spectroscopy includes suspending organic material in a medium to form a sample; irradiating the sample with an illumination beam of electromagnetic radiation, the illumination beam having a plurality of frequencies in the range of about 100 GHz to about 2 THz; detecting radiation transmitted through and/or reflected from the sample; and, analyzing the detected radiation to identify the organic material, wherein the medium is selected from the group consisting of agar, guar gum, gellan gum, carrageenan, xantham gum, fibrous sodium pectate, and other agar substitutes.

17 Claims, 5 Drawing Sheets

METHOD OF DETECTING ORGANIC MATERIALS USING TERAHERTZ SPECTROSCOPY

BACKGROUND OF THE INVENTION

1. Field of the Invention

The invention relates generally to methods of detecting organic material, and more particularly to a method of detecting organic material using terahertz spectroscopy.

2. Description of the Related Art

Spectroscopy over the terahertz (THz) region may be divided into two basic techniques: time-domain and frequency-domain. Time domain systems employ optical pulses from a mode locked laser to produce THz pulses through a demodulation process in a photo-conductive (i.e., "Auston") switch (PCS). The THz pulse is passed through the sample of interest before being focused onto a second PCS (the detector) that is driven by a delayed optical pulse from the same mode locked laser. The delay of this optical detector pulse is varied; and the detector PCS photocurrent is measured as a function of delay to obtain a THz autocorrelation function. A normalization and Fourier transformation are applied to this autocorrelation to produce a frequency-dependent transmission through the sample of interest. As in Fourier Transform spectroscopy, the spectral resolution is determined primarily by the length of the delay line, which is very difficult to increase much past 1 cm, rendering a typical resolution of 1 $cm^{-1}$ or 30 GHz.

In the frequency-domain technique, on the other hand, continuous-wave THz radiation is produced through photomixing of the combined output of two single-frequency lasers in a PCS. The wavelength of one (or both) of the lasers is tuned to vary the THz output frequency. In most spectroscopic applications of photomixing, the THz output beam from the PCS is coupled to a sensitive broadband thermal detector (e.g., LHe bolometer or Golay cell), making the overall signal processing incoherent and phase insensitive. Coherent (homodyne) detection can be achieved at room temperature by mixing the same optical radiation from the lasers in a detector PCS onto which the THz signal is also incident. This provides greater sensitivity and faster data acquisition than the incoherent technique, and preserves phase information.

Some of the benefits of the coherent frequency-domain technique compared to the time-domain technique are no moving parts, higher frequency resolution, the ability to selectively scan specific frequency regions of interest with adjustable resolution, the potential to highly integrate the inexpensive semi-conductor laser chips into an extremely small form factor package and low current requirements that may allow battery operation. Also, unlike pulsed systems, CW photomixing results in all of the THz power being concentrated at a single THz frequency, thus improving spectral density and signal-to-noise ratio at that frequency.

Despite the advantages, historically, it has been difficult to realize compact frequency-domain spectrometers due to the challenges associated with the construction and control of the dual lasers, namely mode-matching and co-collimation of the two laser beams and precise control of their difference frequency.

SUMMARY OF THE INVENTION

Disclosed herein are methods of detecting organic material using terahertz spectroscopy. In accordance with some examples, the methods include suspending organic material in a medium to form a sample, irradiating the sample with an illumination beam of electromagnetic radiation, the illumination beam having a plurality of frequencies in the range of about 100 GHz to about 2 THz, detecting radiation transmitted through and/or reflected from the sample, and analyzing the detected radiation to identify the organic material, wherein the medium is selected from the group consisting of agar, guar gum, gellan gum, carrageenan, xantham gum, fibrous sodium pectate, and other agar substitutes. Preferably, the medium is agar.

Preferably, the plurality of frequencies is in the range of about 400 GHz to about 700 GHz. In another embodiment, the plurality of frequencies is in the range of about 500 GHz to about 800 GHz. The method may further include applying electric poling to the sample. The method may also include irradiating the sample in a dry box.

In some embodiments, the organic material is a carbohydrate. The organic material may be a monosaccharide or a disaccharide. The organic material may be a disaccharide selected from the group consisting of sucrose, lactulose, lactose, maltose, trehalose, cellobiose, and mixtures thereof. Preferably, the organic material is lactose.

The method may further include performing a baseline comparison with a medium sample, without the organic material, including irradiating the medium sample with the illumination beam; detecting radiation transmitted through and/or reflected from the medium sample; and, comparing the detected radiation of the medium sample to the detected radiation of the sample. The method may further include performing a baseline comparison with air including irradiating air with the illumination beam; detecting radiation transmitted through and/or reflected from air; and, comparing the detected radiation of air to the detected radiation of the sample.

The method may further include performing a weighted average sample by irradiating and detecting the radiation from the sample more than one time.

In one embodiment, the illumination beam is a time-domain, pulsed illumination. In another embodiment, the illumination beam is a frequency-domain, continuous illumination.

The method may further include generating a composite laser beam in an integrated laser module; and applying the composite laser beam to a first photoconductive switch activated by the composite laser beam to form the illumination beam as an optically-generated illumination beam. The method may include applying the composite laser beam to a detector positioned for detecting the radiation transmitted through and/or reflected from the sample, wherein said detector comprises a second photoconductive switch activated by the composite optical beam. The method may include generating the composite laser beam from first and second lasers with different frequencies, each modulated with a different low frequency identification tone.

BRIEF DESCRIPTION OF THE DRAWINGS

These and other features and advantages of this invention will be better understood and more fully appreciated by reference to the following detailed description when considered in conjunction with the accompanying drawings wherein.

Figure 1:
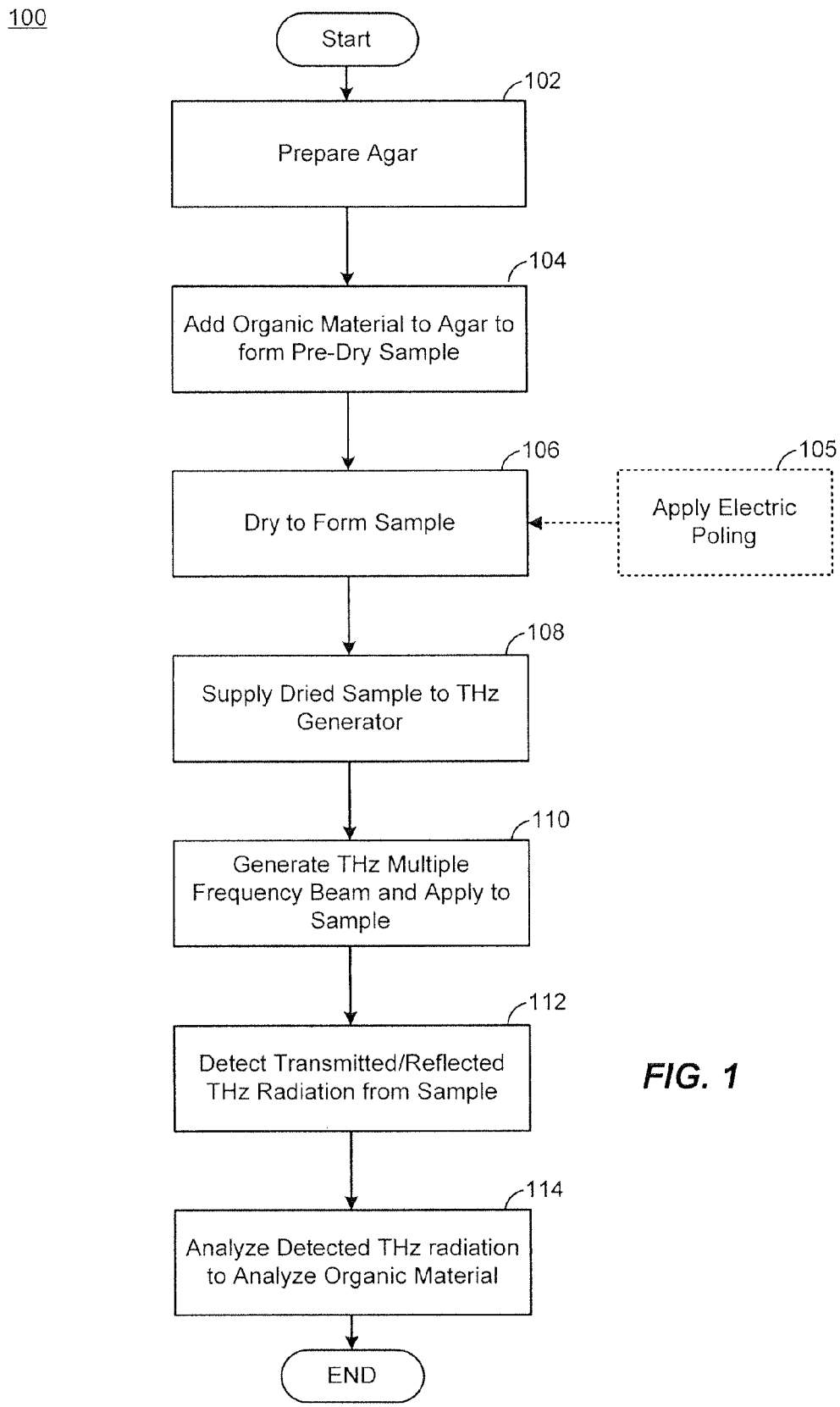
FIG. 1 illustrates a process for detecting organic materials using THz spectroscopy.

The novel features and characteristics of the invention are set forth in the appended claims. The invention itself, however, as well as other features and advantages thereof, will be best understood by reference to a detailed description of example embodiments, when read in conjunction with the accompanying drawings.

DETAILED DESCRIPTION

Described herein are methods of detecting organic material using THz spectroscopy, wherein the organic material is suspended in a medium. The medium can be selected from the group consisting of agar, guar gum, gellan gum, carrageenan, xantham gum, fibrous sodium pectate, acrylamide, and other agar substitutes. The medium can be a film-forming polysaccharide. Preferably, the medium is agar.

Agar has been used in microbiology to provide a solid surface containing medium for the growth of bacteria. Agar is a heterogeneous mixture of two classes of polysaccharide: agarose and agaropectin, which share the same galactose-based backbone. The neutral charge and lower degree of chemical complexity of agarose make it less likely to interact with biomolecules.

Suspending the organic material to be detected in agar stabilizes the organic material for effective THz spectroscopy. While not being bound by theory, it is believed that the agar enables detection of intramolecular vibrational modes and intermolecular vibrational modes.

Using this method, many types of organic material can be analyzed. Organic material is any chemical compound that contains carbon. Organic compounds can be either natural or synthetic. Natural compounds refer to those made by plants or animals, such sugars, or simple carbohydrates.

The organic material is preferably a carbohydrate. Carbohydrates are simple organic compounds that are aldehydes or ketones. Carbohydrates have four chemical groupings: monosaccharides, disaccharides, oligosaccharides, and polysaccharides. The basic carbohydrate units are monosaccharides, such as glucose, galactose, and fructose. Common disaccharides, which are formed of two monosaccharides, include sucrose, lactulose, lactose, maltose, trehalose, and cellobiose. An oligosaccharide is a polymer formed of a small number of monosaccharides. Polysaccharides are polymeric carbohydrate structures, formed of repeating units of either monosaccharides or disaccharides, joined together by glycosidic bonds. Some common polysaccharides include starches, glycogen, cellulose, and chitin.

Preferably, the organic material is a carbohydrate, more preferably a monosaccharide or disaccharide, and most preferably a disaccharide. In preferred embodiments, the organic material can be a disaccharide selected from the group consisting of sucrose, lactulose, lactose, maltose, trehalose, cellobiose, and mixtures thereof.

The sample, i.e., the medium with the organic material, may be dried. The drying process preferably removes the majority of the water from the sample. Drying processes, for example, may include chemical drying, applying a vacuum, ambient drying, or applying heat. In a preferred embodiment, the drying process removes substantially all of the water from the sample.

FIG. 1 illustrates an example process 100 for detecting organic material using THz spectroscopy by suspending the material in agar. While the example is discussed with respect to suspension in agar therein, it will be appreciated that any type of suitable medium may be used. At block 102, the agar is prepared. For example, a certain amount of agar is added to water, boiled, and allowed to cool. At block 104, before the agar has cooled completely, the organic material is dissolved or suspended in the agar, and mixed to ensure uniformity. At optional block 105, after the organic material is dissolved or suspended in the agar, the still unset agar with the organic material can be subjected to an electric poling process.

Common poling processes include, for example, contact poling and corona poling. For example, in contact poling, the sample is placed between two electrodes applying the poling electric field. The sample may be contained within a housing while drying but otherwise not confined. In corona poling, a large electric field is applied between a needle positioned over the sample and a ground plane on the other side of the sample. The large electric field creates a corona discharge between the needle and the sample. Ions build up on the surface of the sample and create a very strong electric field across the sample that poles the organic material in the sample.

In general, poling may be achieved at or below room temperatures or in some examples above room temperature. Merely by way of example, and not limitation, poling fields may be from about 40 to 150 V/micrometer.

The poling technique and parameters used in aligning the dipoles of the organic material in the agar can be matched to the particular temperature desired for drying. For a dried sample, the poling may be applied by gradually raising the temperature of the sample while poling, and in some examples simultaneously raising the poling field.

The poling process aligns the dipoles of the molecules in the organic material, and as the medium sets and dries, the molecules are locked in the aligned position. By controlling the applied electric field, the sample can be controlled to affect the resulting waveform of the transmitted terahertz beam. In this way, electric poling can be used to improve THz spectroscopic analysis, by controlling terahertz waveforms and overall process efficiency.

Electric poling is preferably applied throughout the setting and drying of the agar. Electric poling may be applied in a continuous or pulsed manner and may be applied during a selective portion of the agar drying stage.

In another embodiment, the process 100 may include an electrophoresis process. For example, once the medium has cooled and set, the organic material can be placed in or on the medium. An electric field may be applied, and the organic material will migrate through the medium. The medium may then be dried, locking the aligned organic material in the medium. If the organic material is not uniform, the electrophoresis process may separate the components of the organic material within the medium by size or charge.

Returning to FIG. 1, at block 106, the agar with the suspended organic material is dried to form a sample. The agar will set at room temperature. However, optional drying techniques, such as applying heat or electrohydrodynamic drying, may improve drying and ultimately improve the THz analysis. At block 108, the sample is provided to the THz spectroscopy system. This sample can be taken from a larger production volume and provided to the THz system via a delivery mechanism such as a vial, Petri dish, glass plate, etc. The sample can be provided through manual or automatic means, and continuously fed or periodically sampled, for example in a batch-wise manner. In a continuous mode, samples can pass by the detector continuously, with the detector irradiating the passing samples. At block 108, the sample can optionally be provided to a dry box to minimize detection of the water vapor transitions.

At block 110, THz radiation is generated by the spectroscopy system that is used to spectrally examine the sample from block 106. The apparatus detects the radiation transmitted through and/or reflected from the sample at block 112, where a THz frequency detector collects the transmitted through and/or reflected radiation and converts it to the appropriate data. The detector may be of various types, including a scanning THz detector or array traditionally used for THz imaging. Preferably, the detector is an intensity detector.

At block 114, analyzes the detected radiation to determine the absorbance, and thus, the chemical content of the sample, in particular whether the sample has any one of a number of identifiable containments. Various methods of analysis may be executed by the block 114, including comparing the detected radiation values from block 112 to known radiation profiles of organic material, or baselining the detected radiation values against a pure (without organic material) sample of the agar. For the former, the radiation detected can be compared to a known library of organic material (e.g., stored in a look-up table or other data memory storage form) to determine which organic material is present. The latter may include obtaining a characteristic absorbance spectrum of the pure agar as a baseline. Then, the baseline from the pure agar can be subtracted out of the detected radiation from the sample to determine which organic material is present. In some examples, the block 114 may also determine a quality, or assurance, factor that analyzes the quality of the detected radiation data and providing a separate indication of sample data accuracy, which can change depending on noise in the detection radiation signal, intensity variations across the spectral region, and other operational conditions.

Because in the preferred examples the process 100 is non-destructive, the same sample can be tested numerous times, such that the analysis block 114 may average detected radiation data over multiple tests of the same sample or over multiple tests taken of different samples from the same production volume. Averaging the data will help reduce noise. More robust analysis techniques, including the partial least-squares (PLS) models of Mauer et al., J. Agric. Food Chem. 57:3974-3980 (2009) may be modified to develop correlation models between THz spectroscopic data and the type of organic material.

The THz beam generated by block 110 includes a plurality of frequencies in the range of about 100 GHz to about 2 THz, and preferably in the range of about 400 GHz to about 700 GHz, or in the range of about 500 GHz to about 800 GHz. An example THz beam generator and spectroscopy system will now be described.

Figure 2:
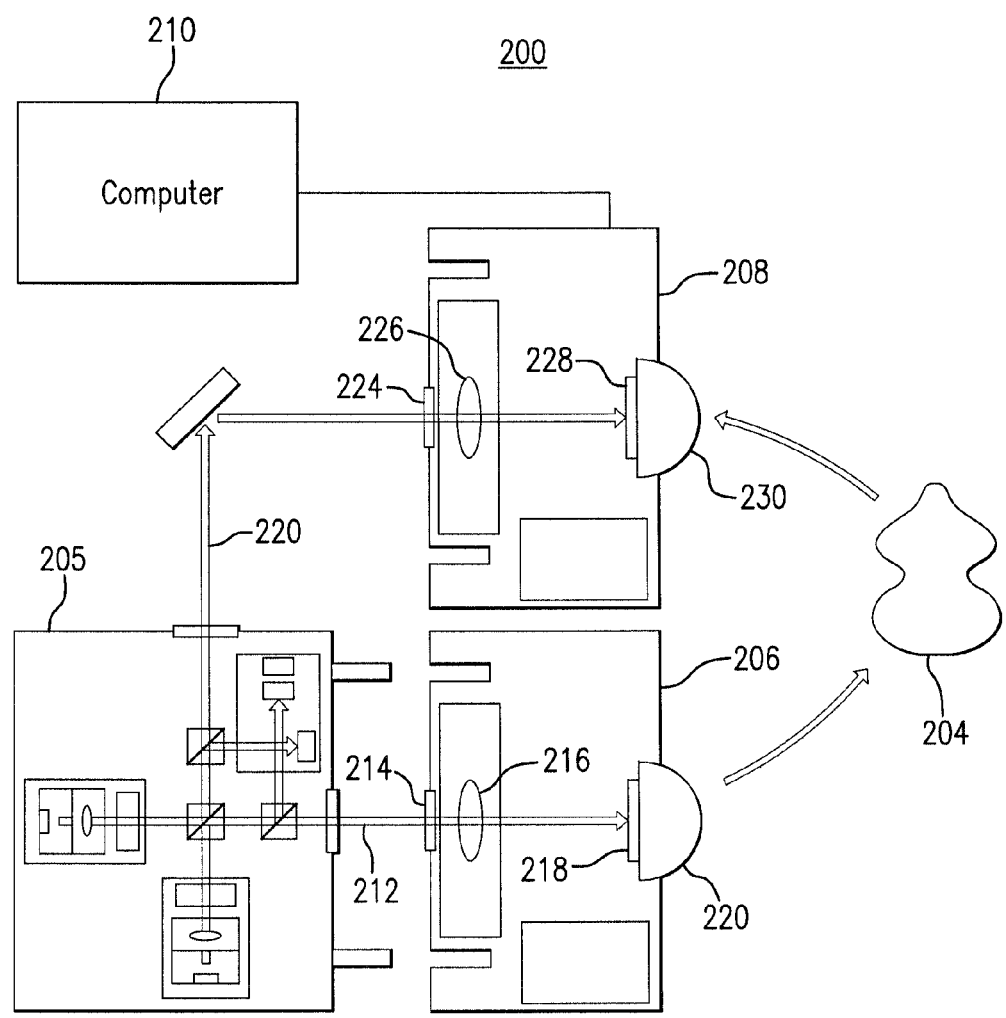
FIG. 2 is a block diagram of a THz spectrometer that may be used to implement the process of FIG. 1 and that is able to achieve desired detection levels at low terahertz frequencies.

FIG. 2 is a simplified block diagram that illustrates the integration of the dual laser module 205 into a spectrometer system 200 for implementing the process 100. In general, the spectrometer system 200 may employ reflection or transmission through the sample 204 by appropriate placement of a THz source head 206 and a THz detector head 208. Furthermore, the system 200 includes a computer 210, e.g., having a processor and other electronics, for determining the identity or composition of the target, and/or printing or displaying the results so that the information is readily available to the user.

In the illustrated dual laser module configuration, a primary laser beam 212 is coupled to a window 214 in the appropriately positioned source head 206, and then coupled to a lens 216 that focuses the beam 212 to a spot of approximately ten microns in diameter on the surface of a PCS 218. The optical frequency signal directed to the surface of the PCS semiconductor device produces THz radiation from the PCS 218 in the frequency range 100 GHz to over 2 THz, corresponding to the offset frequency between the lasers in dual laser module 205. The THz radiation emitted from the PCS device 218 is collimated and collected by a silicon lens 220 mounted to the source head 206. The lens 220 is preferably a hemispherically shaped structure approximately one centimeter in diameter. Additional lenses (not shown), composed of Teflon may be placed downstream of the lens 220 to collimate the RF beams into the output THz beam. Beam-shaping mirrors may also be used in lieu of or in addition to the silicon lens. The sample 204 will absorb and transmit some radiation, and in the illustrated example also reflect a portion of the radiation back in the direction of the source or user.

A secondary beam 220 from dual laser module 205 is directed to the detector head 208. The secondary beam 220, for example, is coupled to a window 224, and then coupled to a lens 226 that focuses the beam to a spot of approximately ten microns in diameter on the surface of a PCS 228. A silicon lens 230 collects transmitted or reflected radiation from the sample 204, which is then detected by PCS 228, and processed by the computer 210.

Thus, FIG. 2 illustrates an example THz spectroscopy system that may be used for detection as discussed in example process of FIG. 1. Generally speaking, this system is implemented using two ErAs:GaAs PCSs in a highly compact configuration, utilizing all solid-state components and no moving parts. The system utilizes a single package integration of two 783 nm DFB laser diodes with a high-resolution wavelength discriminator. Digital signal processing electronics can provide precise frequency control and yield approximately 200 MHz accuracy of the THz signal frequency. Continuous frequency sweeping has been demonstrated with better than 500 MHz resolution from 100 GHz to 1.85 THz, thus making better resolution spectral data for analysis. The coherent detection sensitivity is shown to be in good agreement with previous theoretical predictions and yields a signal-to-noise ratio of 90 dB/Hz at 100 GHz and 60 dB/Hz at 1 THz through a path length in air of one foot. The spectrometer frequency resolution and dynamic range are suitable for applications involving analysis of chemical, biological, and explosive materials in solid-phase and gas-phase at atmospheric pressure.

The construction employs highly compact photonic integration techniques, electronic differential chopping, and room-temperature coherent THz detection. The highly integrated photonic assembly employing semiconductor diode lasers employs no moving parts and is inherently rugged and well-suited to field-deployable applications. Also, the coherent (homodyne) detection technique provides excellent SNR in agreement with theory, with much faster data acquisition times and no cryogenic cooling as required by the liquid helium bolometers in more common (incoherent) THz photomixing spectrometers.

While a frequency-domain THz spectroscopy system is described, other THz spectroscopy systems may be used instead for organic material detection. These include time domain THz spectroscopy systems, for example those using a mode locked laser, (e.g., Ti:Sapphire laser or solid state laser) capable of producing a sequence of femtosecond pulses that are focused onto suitable semiconductor material to produce THz radiation. The THz signals produced by the optical pulses typically peak in the 0.5-2 THz range and have average power levels in the microwatt range and peak energies around a femtojoule. In some examples, the mode locked pulsed laser beam may be split and synchronized through a scanning optical delay line and made to strike a THz generator material (emitter) and a detector in known phase coherence. By scanning a delay line and simultaneously gating or sampling the THz signals incident on the detector, a time-dependent waveform proportional to the THz field amplitude is produced. Once generated, the THz radiation is directed to the sample 204 to be analyzed, and the detector or detector array is used to collect the signal propagated through or reflected from the object. Such measurements are made in the time domain by collecting the timed sequence of pulses and then processed by a Fourier transformation to recover the frequency domain spectral information.

In either type of system, the THz spectroscopy system is able to examine a particular location on the sample 204 or be designed as a scanning system that scans every point or "pixel" on the sample 205, either on a focal plane or in successive focal planes at different ranges. This may be particularly useful for detecting organic material, in case the organic material was not homogeneously incorporated, because the THz radiation from the system 200 could be focused to or scanned over particular locations for targeted analysis.

This method can be used to identify an unknown organic material, having a unique THz spectrum that can be identified using the disclosed methods. Furthermore, when the organic material, and its unique THz spectrum, is known, this method can enable detection of contaminants in that known organic material. The use of the medium to suspend the organic material allows for the stabilization of the material, including the contaminant. Electric poling can improve the analysis of the organic material.

Further, this method enables the testing of liquids and powders that can be dissolved in the medium. Liquid samples tend to be problematic in THz spectroscopy because of the high concentration of water, which exhibits high absorption over the THz spectrum. For example, 1 mm thick of liquid water normally entirely attenuates the radiation in the THz frequency range. Agar, surprisingly, contributes very little to signal reduction, and therefore, provides an effective medium for testing organic material.

EXAMPLES

The THz spectrometer was employed to study a low-frequency vibrational mode in lactose monohydrate in both a pure powder form and in a "dissolved" form suspended in an agar matrix.

THz Spectrometer Characterization

Figure 3:
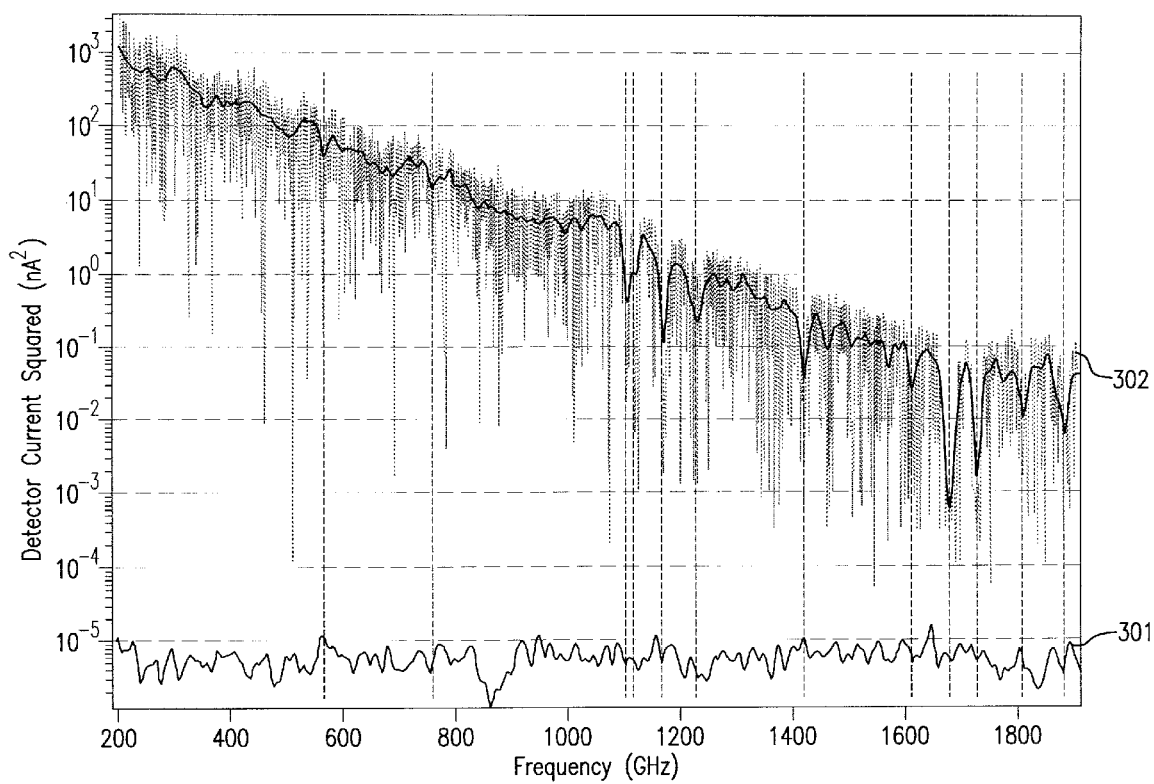
FIG. 3 is a graph characterizing a THz spectrometer configured as shown in FIG. 2.

Using a THz spectrometer like the one detailed in FIG. 2, the signal-to-noise ratio ("SNR") was measured, as shown in FIG. 3. The bottom trace (301) is the power spectrum with the THz beam is blocked. The top trace (302) shows the detected power spectrum for a 30 centimeter (cm) path length in air with a 1 GHz frequency resolution and 1 second integration time. The signal (302) is shown with (black) and without (gray) a 25-point smoothing function applied. The rapid variation in the unsmoothed signal power versus frequency is expected, and is due an interferometric effect caused by the significantly different lengths of the laser-to-photo-mixer arms of the spectrometer.

Smoothing removes this interferometric effect but also discards the phase information contained within. The signal-to-noise ratio of ~80 dB/Hz obtained at 200 GHz is consistent with the theoretical prediction. The SNR improvement is attributed mostly to improved optical beam collimation and overlap in the integrated laser assembly, and improved optical and THz coupling of the present instrument. The dashed vertical lines indicate the frequencies of the strongest water vapor absorptions.

Comparative Example

Figure 4:
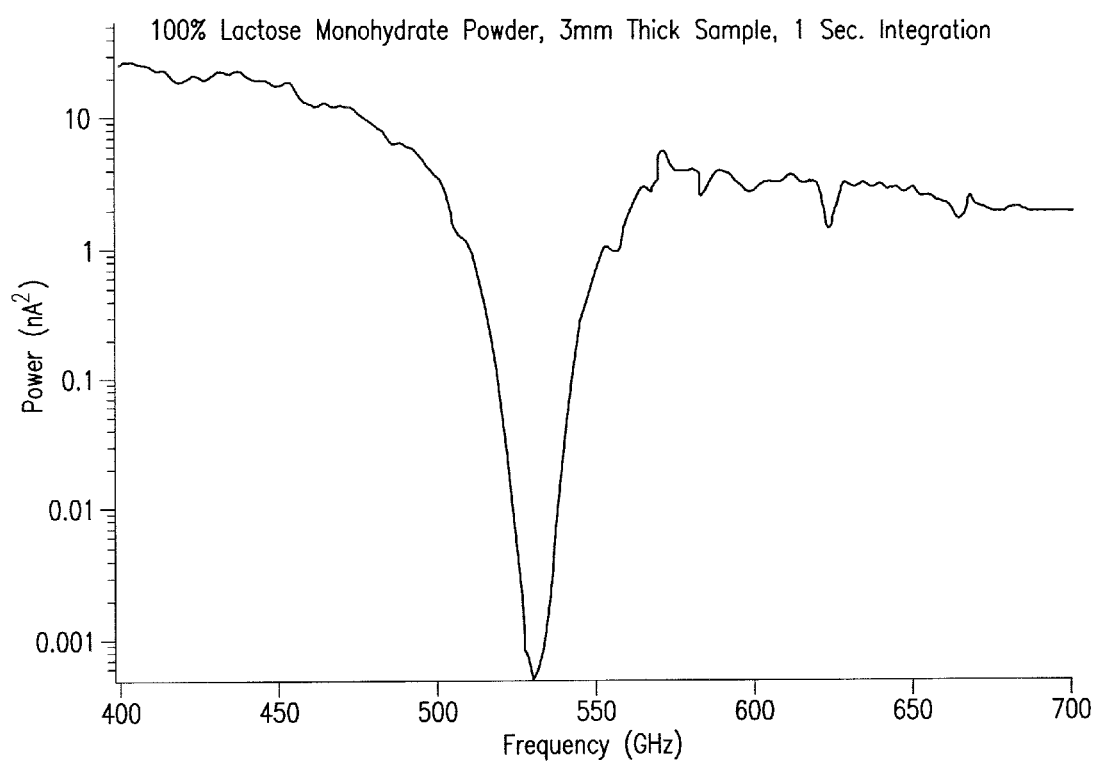
FIG. 4 is a graph of the THz spectrum (power vs. wavelength) for lactose powder alone; and, FIG. 5 is a graph of the THz spectrum (power vs. wavelength) for air, agar, and agar with lactose under an example application of the THz spectrometer of FIG. 3.

A powdered lactose monohydrate sample was placed in the center of a large, metal washer, which had clear plastic adhesive tape on the back side. After the powder was distributed in the washer, clear plastic adhesive tape was placed over the sample holding it in place and setting the sample thickness to 3 mm. The frequency domain THz spectrometer, as detailed in FIG. 2, was then employed to measure the lowest frequency absorption feature in the lactose monohydrate powder. The THz spectrum was generated with a 500 MHz resolution and 1 second integration time. The five-decade dynamic range of the THz spectrometer at these frequencies is clear and makes it possible to easily determine the full-width half-maximum of the absorption feature which is approximately 25 GHz and occurs at roughly 535 GHz, as shown on FIG. 4. While the weak 620 GHz water vapor transition is present, the typically much stronger 557 GHz transition is masked by the broad lactose monohydrate transition.

Example 1

Figure 5:
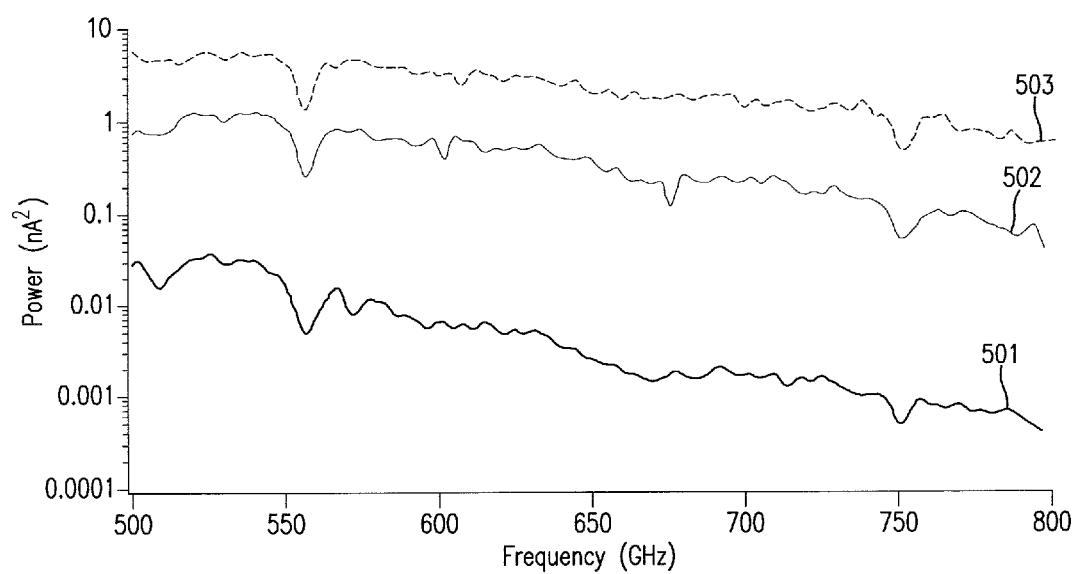

A mixture of 2 grams of biological grade agar was briefly boiled in 40 ml of water to establish cross-linking and then allowed to dry under a low speed fan. Such a technique produced an agar film approximately 0.5 mm thick upon drying. For the lactose-containing sample, 2 grams of biological grade agar was briefly boiled in 40 ml of water, and allowed to cool. Before the agar had completely cooled, 4 grams of lactose monohydrate was added to the mixture and mixed. FIG. 5 illustrates a comparison between a single background scan of air (503), a scan of the pure agar film (502), and a scan of the agar film containing lactose monohydrate (501). The THz spectrum was generated with a 500 MHz resolution and 1 second integration time.

There is a relatively low loss of 7 dB for the dried agar matrix. In comparison, a 1 mm thick sample of liquid phase water would normally entirely attenuate the radiation in this frequency range. Clearly, the majority of the water has been removed from the agar and it is believed that the current 7 dB of attenuation is due to the water that is still present. The sample containing the lactose monohydrate displays 15 to 20 dB of loss. This loss may be minimized with improved drying techniques. Because the measurements were performed in the ambient environment, the typical 557 and 752 GHz water vapor transitions are present on all the traces. The agar sample (502) also displays features at 605 and 676 GHz. The agar and lactose sample (501) appears to have a narrow feature at 571 GHz and a broader feature centered at 670 GHz. The waterline at 557 GHz also appears to be slightly broadened in the agar and lactose sample (501). While not being bound by theory, it is believed that this may be due to the presence of an unresolved lactose monohydrate feature. These features of the sample containing agar and lactose enable analysis of the entire THz spectrum, as compared to the lactose powder alone in the example above.

Various modifications and improvements of the present invention may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

Various aspects of the techniques and signal processing apparatus of the present invention may be implemented in digital circuitry, or in computer hardware, firmware, software, or in combinations of them. Circuits of the invention may be implemented in computer products tangibly embodied in a machine-readable storage device for execution by a programmable processor, or on software located at a network node or web site which may be downloaded to the apparatus automatically or on demand. The foregoing techniques may be performed by, for example, a single central processor, a multiprocessor, one or more digital signal processors, gate arrays of logic gates, or hardwired logic circuits for executing a sequence of signals or program of instructions to perform functions of the invention by operating on input data and generating output. The methods may advantageously be implemented in one or more computer programs that are executable on a programmable system including at least one programmable processor coupled to receive data and instructions from, and to transmit data and instructions to, a data storage system, at least one in/out device, and at least one output device. Each computer program may be implemented in a high-level procedural or object-oriented programming language, or in assembly or machine language if desired; and in any case, the language may be compiled or interpreted language. Suitable processors include, by way of example, both general and special purpose microprocessors. Generally, a processor will receive instructions and data from read-only memory and/or random access memory. Storage devices suitable for tangibly embodying computer program instructions and data include all forms of non-volatile memory, including by way of example, semiconductor devices, such as EPROM, EEPROM, and flash memory devices; magnetic disks such as internal hard disks and removable disks; magneto-optical disks; and CD-ROM disks. Any of the foregoing may be supplemented by or incorporated in, specially designed application-specific integrated circuits (ASICS).

It will be understood that each of the elements described above, or two or more together, also may find a useful application in other types of constructions differing from the types described above.

The foregoing description is given for clearness of understanding only, and no unnecessary limitations should be understood therefrom, as modifications within the scope of the invention may be apparent to those having ordinary skill in the art.

The invention claimed is:

1. A method of detecting organic material using terahertz spectroscopy, the method comprising:
    suspending organic material in a medium to form a sample;
    generating a composite laser beam in an integrated laser module;
    applying the composite laser beam to a first photoconductive switch activated by the composite laser beam to form an illumination beam as an optically-generated illumination beam;
    irradiating the sample with the illumination beam of electromagnetic radiation, the illumination beam having a plurality of frequencies in the range of about 100 GHz to about 2 THz;
    detecting radiation transmitted through and/or reflected from the sample; and,
    analyzing the detected radiation to identify the organic material,
    wherein the medium is selected from the group consisting of agar, guar gum, gellan gum, carrageenan, xantham gum, fibrous sodium pectate, acrylamide, and other agar substitutes.

2. The method of claim 1, wherein the medium is agar.

3. The method of claim 1, further comprising applying electric poling to the sample.

4. The method of claim 1, further comprising irradiating the sample in a dry box.

5. The method of claim 1, wherein the plurality of frequencies is in the range of about 400 GHz to about 700 GHz.

6. The method of claim 1, wherein the plurality of frequencies is in the range of about 500 GHz to about 800 GHz.

7. The method of claim 1, wherein the organic material is a carbohydrate.

8. The method of claim 1, wherein the organic material is a monosaccharide or a disaccharide.

9. The method of claim 1, wherein the organic material is a disaccharide selected from the group consisting of sucrose, lactulose, lactose, maltose, trehalose, cellobiose, and mixtures thereof.

10. The method of claim 1, wherein the organic material is lactose.

11. The method of claim 1 further comprising performing a baseline comparison with a medium sample, without the organic material, comprising:
    irradiating the medium sample with the illumination beam;
    detecting radiation transmitted through and/or reflected from the medium sample; and,
    comparing the detected radiation of the medium sample to the detected radiation of the sample.

12. The method of claim 11 further comprising performing a baseline comparison with air comprising:
    irradiating air with the illumination beam;
    detecting radiation transmitted through and/or reflected from air; and,
    comparing the detected radiation of air to the detected radiation of the sample.

13. The method of claim 1 further comprising performing a weighted average sample by irradiating and detecting the radiation from the sample more than one time.

14. The method of claim 1, wherein the illumination beam is a time-domain, pulsed illumination.

15. The method of claim 1, wherein the illumination beam is a frequency-domain, continuous illumination.

16. The method of claim 1, further comprising applying the composite laser beam to a detector positioned for detecting the radiation transmitted through and/or reflected from the sample, wherein said detector comprises a second photoconductive switch activated by the composite optical beam.

17. The method of claim 1, further comprising generating the composite laser beam from first and second lasers with different frequencies, each modulated with a different low frequency identification tone.

* * * * *